(12) United States Patent
Pelland

(10) Patent No.: US 10,729,594 B2
(45) Date of Patent: *Aug. 4, 2020

(54) FEMININE HYGIENE PRODUCTS AND APPARATUS AND METHODS FOR MAKING DISPOSABLE PRODUCTS

(71) Applicant: Curt G. Joa, Inc., Sheboygan Falls, WI (US)

(72) Inventor: Jon Allen Pelland, Sheboygan, WI (US)

(73) Assignee: Curt G. Joa, Inc., Sheboygan Falls, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/386,495

(22) Filed: Apr. 17, 2019

(65) Prior Publication Data

US 2019/0269559 A1 Sep. 5, 2019

Related U.S. Application Data

(63) Continuation of application No. 15/331,342, filed on Oct. 21, 2016, now Pat. No. 10,307,301.

(Continued)

(51) Int. Cl.
| | |
|---|---|
| *A61F 13/15* | (2006.01) |
| *A61F 13/56* | (2006.01) |
| *A61F 13/551* | (2006.01) |
| *B29C 65/08* | (2006.01) |
| *B29C 65/48* | (2006.01) |
| *B29C 69/00* | (2006.01) |
| *B29L 31/48* | (2006.01) |

(52) U.S. Cl.
CPC .. *A61F 13/15756* (2013.01); *A61F 13/15699* (2013.01); *A61F 13/15804* (2013.01); *A61F 13/5514* (2013.01); *A61F 13/5616* (2013.01); *B29C 65/08* (2013.01); *B29C 65/48* (2013.01); *B29C 69/001* (2013.01); *B29K 2995/0068* (2013.01); *B29L 2031/4878* (2013.01)

(58) Field of Classification Search
CPC .......... A61F 13/15756; A61F 13/15894; A61F 13/15699; B29L 2031/4878; B29K 2995/0068

See application file for complete search history.

(56) References Cited

U.S. PATENT DOCUMENTS

| | | |
|---|---|---|
| 5,868,727 A | 2/1999 | Barr et al. |
| 6,391,011 B1 | 5/2002 | Davis et al. |

(Continued)

FOREIGN PATENT DOCUMENTS

| | | |
|---|---|---|
| JP | H04300547 A | 10/1992 |
| JP | 2007-105401 A | 4/2007 |

(Continued)

*Primary Examiner* — Mark A Osele
*Assistant Examiner* — Christopher C Caillouet
(74) *Attorney, Agent, or Firm* — Ziolkowski Patent Solutions Group, SC

(57) ABSTRACT

The present invention provides a method and apparatus for increasing the number of articles processed. over a distance traveled in the machine direction of an assembly line. In particular, the orientation of the long dimension of the article is provided transverse to the machine direction, thus processing the articles side-by-side instead of end-to-end.

20 Claims, 5 Drawing Sheets

Related U.S. Application Data

(60) Provisional application No. 62/245,626, filed on Oct. 23, 2015.

(56) References Cited

U.S. PATENT DOCUMENTS

| | | |
|---|---|---|
| 6,447,495 B1 | 9/2002 | Luizzi et al. |
| 7,240,375 B2 | 7/2007 | Martz |
| D626,218 S | 10/2010 | Lundin |
| 7,805,768 B2 | 10/2010 | Martz |
| 7,927,322 B2 | 4/2011 | Cohen et al. |
| 7,941,872 B2 | 5/2011 | Martz |
| 7,972,318 B2 | 7/2011 | Nijs et al. |
| 8,042,194 B2 | 10/2011 | Connor |
| 8,366,696 B2 | 2/2013 | Konawa |
| 10,307,301 B2 * | 6/2019 | Pelland .................. B29C 65/48 |
| 2002/0068917 A1 | 6/2002 | VanGompel et al. |
| 2002/0148557 A1 | 10/2002 | Heller et al. |
| 2010/0256585 A1 | 10/2010 | Konawa |

FOREIGN PATENT DOCUMENTS

| | | |
|---|---|---|
| JP | 2008284059 A | 11/2008 |
| WO | 1997031604 A1 | 9/1997 |
| WO | 2011105144 A1 | 9/2011 |
| WO | 2013018436 A1 | 2/2013 |
| WO | 2014208363 A1 | 12/2014 |

* cited by examiner

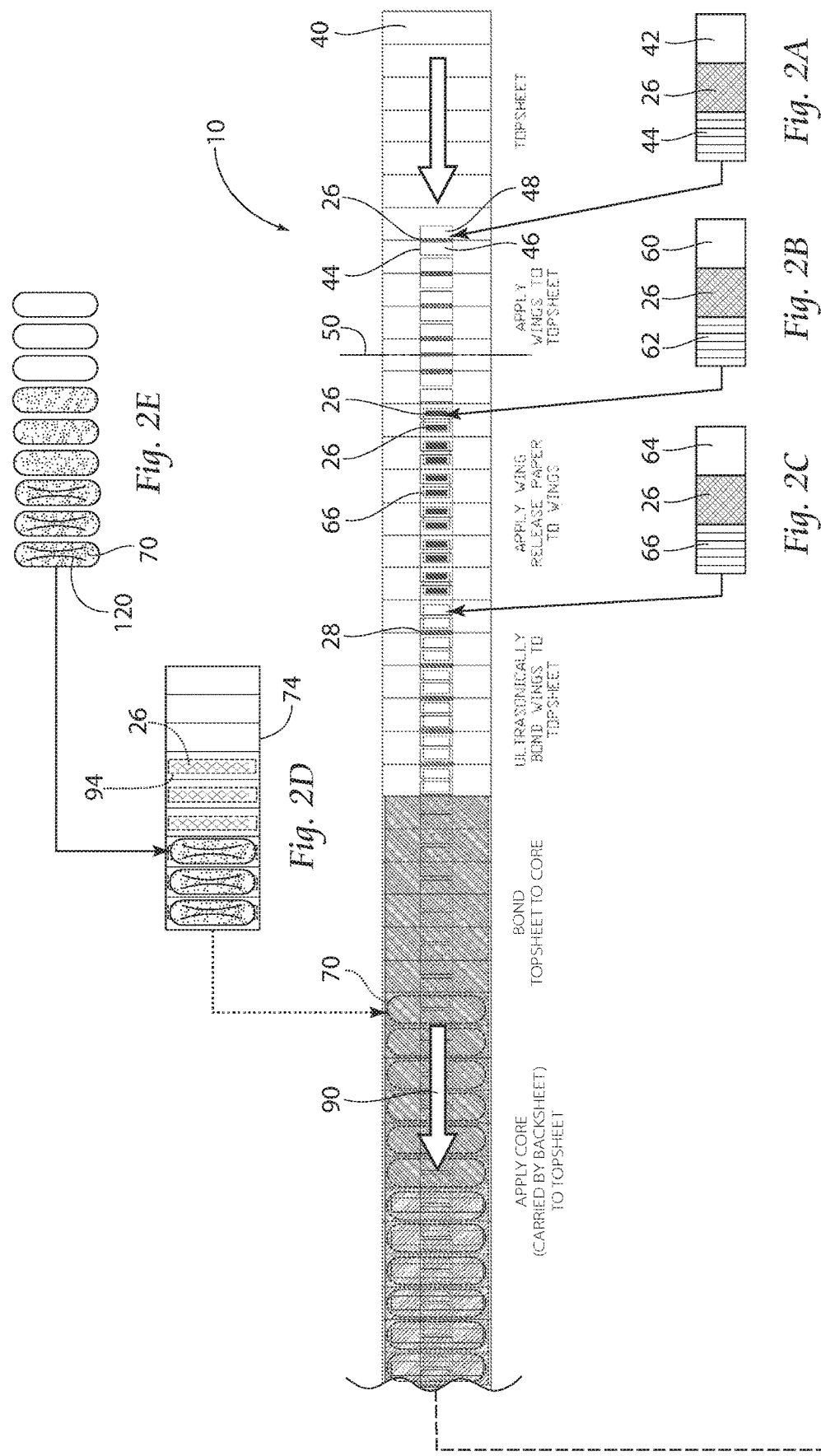

FEMININE HYGIENE PRODUCTS AND APPARATUS AND METHODS FOR MAKING DISPOSABLE PRODUCTS

CROSS-REFERENCE TO RELATED APPLICATIONS

The present application is a continuation of and claims priority to U.S. Non-Provisional patent application Ser. No. 15/331,642, filed 21 Oct. 2016, now U.S. Pat. No. 10,307, 301, which claims priority to U.S. Provisional Patent Application Ser. No. 62/245,626, filed 23 Oct. 2015, the disclosures of which are incorporated herein by reference in their entirety.

BACKGROUND OF THE INVENTION

The present invention relates to processes and apparatus for applying discreet wings to traveling webs as the absorbent articles are oriented transverse to the machine direction.

Generally, the absorbent articles have a long dimension and a short dimension, whereby the articles are oriented along an assembly line with the long dimension in line with the machine direction. As the articles are longer than they are wide, this orientation requires more assembly line space in the machine direction per processed article. The industry could benefit from an alternative approach that would reduce the amount of assembly line space required in the machine direction per processed article to increase the number of articles processed over the same distance traveled through the assembly line, as well as speed.

In prior art sanitary napkin production, right and left wings are often formed of backsheet material, and the right and left wings are folded over the topsheet material and secured to one another for folding and packaging. One example of a prior art sanitary napkin is shown in U.S. Pat. No. 6,391,011. In that patent, a sanitary napkin is shown having flaps placed in a folded disposition prior to use. The flaps are formed of the backsheet material, and the flaps are unitary and coextensive on the product with the backsheet material, so that the backsheet material is folded about side edges of the product to present the flaps for usage and application to an undergarment. A bridge tape extending between the folded over flaps retains the flaps in their folded configuration until use, at which point the bridge tape is removed, exposing adhesive for releasably affixing the sanitary napkin to the undergarment of a wearer.

In the prior art, again as demonstrated by U.S. Pat. No. 6,391,011, absorbent cores are placed on a chassis web with the longer dimension of the core processed and placed onto the chassis web in a machine direction orientation (see, e.g., FIG. 6, U.S. Pat. No. 6,391,011).

SUMMARY OF THE INVENTION

Provided is a method and an apparatus for increasing the number of articles processed aver a distance traveled in the machine direction of an assembly line. In particular, the orientation of the long dimension of the core is provided transverse to the machine direction (cross-machine direction), thus processing the articles side-by-side instead of end-to-end. This results in efficiency of both speed and space. Wing material is placed onto a topsheet in a machine direction, and release papers are applied to the wing material in a relationship advantageous for processing and use, for instance by not requiring folding of the wings over the side edges of the product.

A method of producing a disposable product is disclosed, the method comprising providing a topsheet web of material in a machine direction; coupling a first and a second wing component to said topsheet web on a first side of said topsheet web of material; coupling a first base release paper to said first wing component, coupling a second base release paper to said second wing component, coupling a secondary release paper to said first base release gaper and said second wing component, providing a backsheet web of material in said machine direction, providing an absorbent core having a length dimension and a width dimension, said length dimension greater than said width dimension, between said topsheet and backsheet webs, said length dimension of said core extending in a cross-machine direction, and coupling said topsheet and backsheet webs about said absorbent core.

Said absorbent core is positioned underlying said first and said second wing components, and the method may further comprise severing said first and second wing components to create a first discrete disposable product. Backsheet release paper is releasably to an underside of said backsheet web.

A method of producing disposable products, the method comprising coupling a plurality of wings to a top side of a topsheet web, said topsheet web traveling in a machine direction; releasably coupling a first release paper to a first edge portion of each of said wings; releasably coupling a second release paper to said first release caper and to a second portion of an adjacent wing; providing a series of spaced cores having a length dimension, and a width dimension less than said length dimension, said length dimension oriented transversely to said machine direction; sandwiching said cores between an underside of said topsheet and a top side of a backsheet traveling in said machine direction; bonding said topsheet, and said backsheet; severing said topsheet and said backsheet between spaced cores to produce an absorbent article.

BRIEF DESCRIPTION OF THE DRAWINGS

FIGS. 2-1 and 2-2 are a flow diagram of a process according to the present invention.

FIGS. 2A-2E show a flow diagram of sub-processes of the present invention, FIG. 2A shows wing material being provided, FIG. 2B shows first wing-release paper web formation, FIG. 2C shows second wing release paper formation, FIG. 2D shows a backsheet web receiving adhesive and the combination supplied with cores formed, fluffed, debulked and embossed as shown in FIG. 2E.

DESCRIPTION OF THE PREFERRED EMBODIMENT

Figure 1:
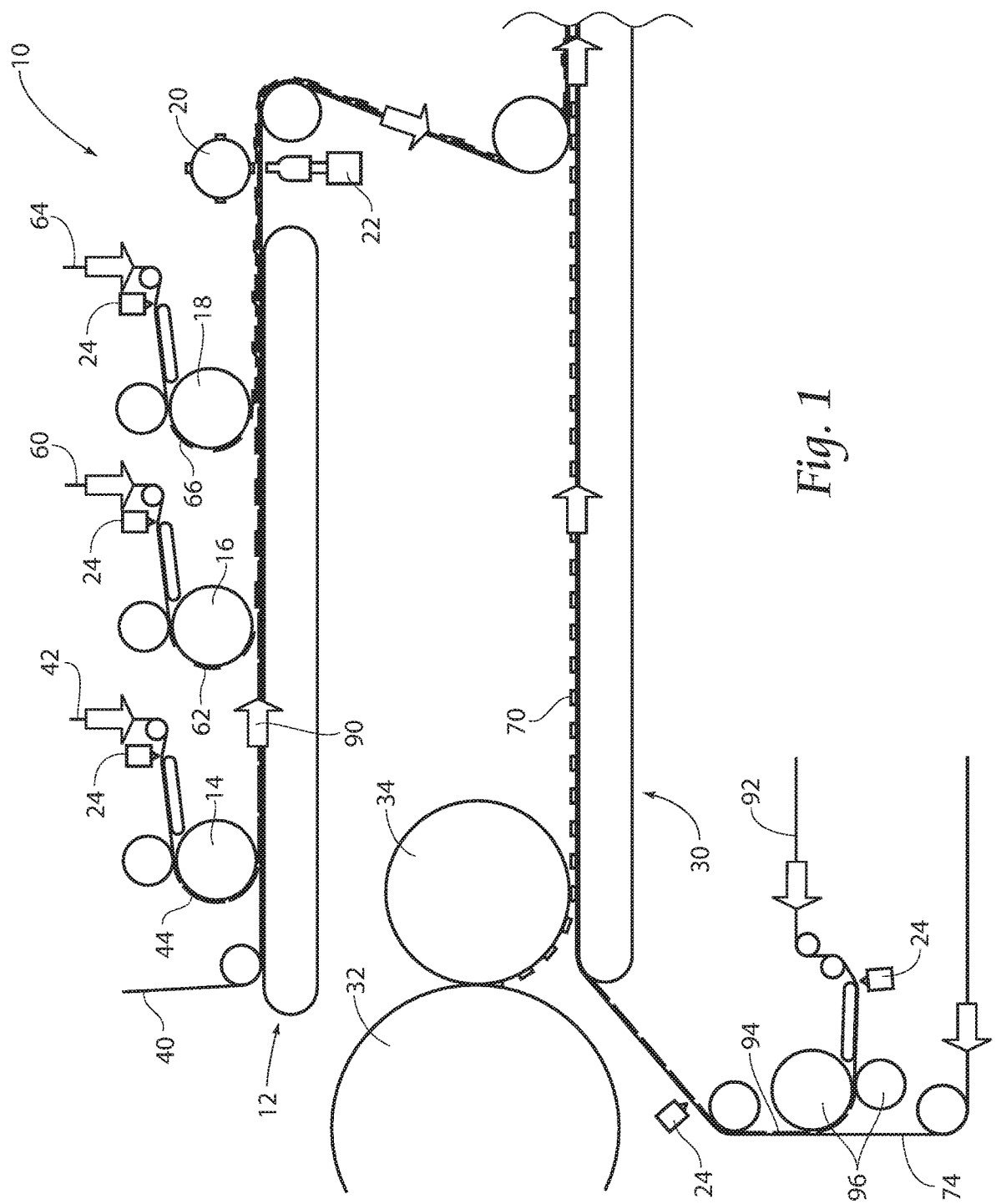
FIG. 1 is a schematic of an apparatus according to the present invention.

Referring now to FIG. 1, an illustration of an apparatus 10 according to the present invention is shown. The apparatus 10 preferably includes a first assembly line 12 comprising a wing die-cutter 14, a first release-paper slip-cutter 16, a second release-paper slip-cutter 18, an anvil 20, an ultrasonic horn 22, and a plurality of adhesive applicators 24, and a second assembly line 30 comprising a core forming drum 32, a core applying drum 34, and an adhesive applicator 24. Adhesives used in the product could include garment adhesive, fugitive adhesive (or transport adhesive), and construction adhesive (for instance for bonding the core to the backsheet). Cores will be placed onto construction adhesive Placed on the backsheet.

Although a first and a second release-paper slip-cutter 16, 18 are shown and discussed, it is contemplated that one release-paper slip-cutter could be provided to perform the steps of the first and the second release-paper slip-cutters 16 18.

Figure 2:
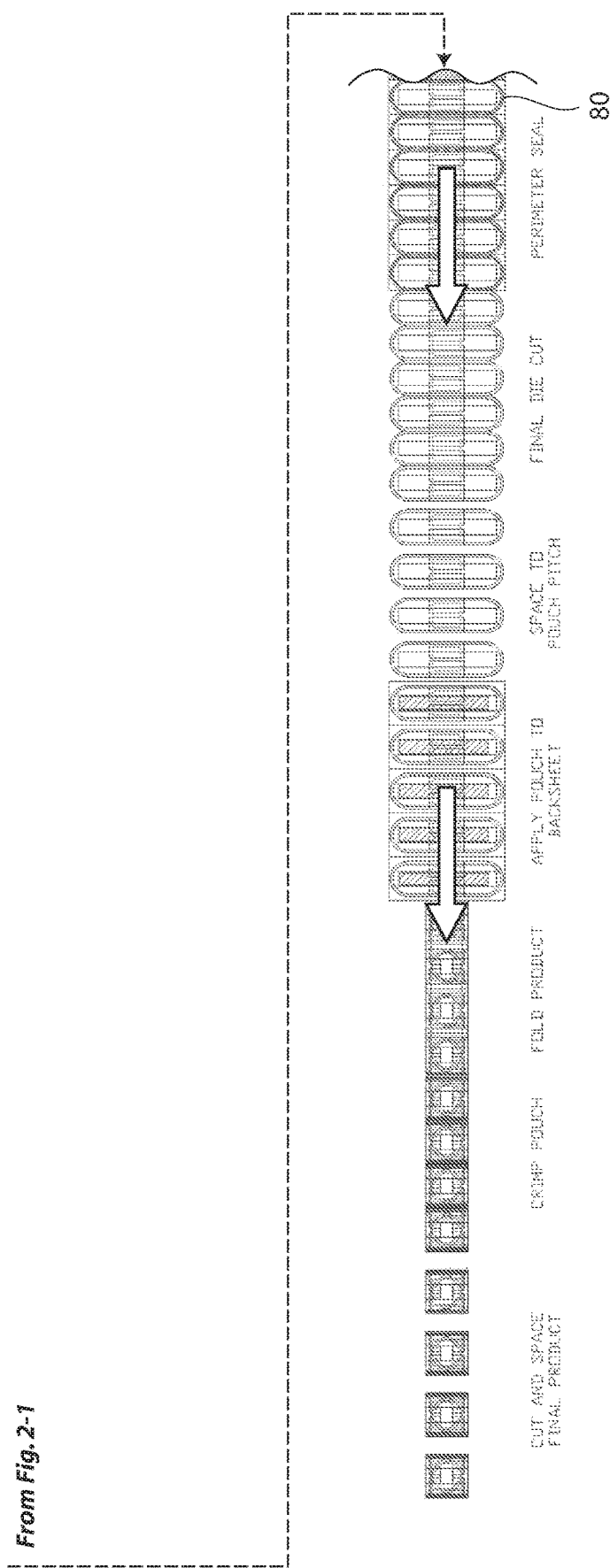

Looking to FIGS. 1 and 2 a process of forming an absorbent article 100 (FIG. 4) according to the present invention is shown. A topsheet 40 is provided at the first assembly line 12 and travels along the first assembly line 12 in a machine direction 90. Wing material 42 receives adhesive 26 (which can be a temporary, or fugitive adhesive indicated as 26') from one of the adhesive applicators 24. The wing material 42 is then processed through the wing die-cutter 14 to provide individual wing members 44 (as shown in FIG. 2A) having a first wing member portion 46 and a second wing member portion 48, with the adhesive 26 dividing the first and second wing member portions 46, 48. Each wing member 44 is then applied to the topsheet 40 as shown Preferably adhesive 26' carried by wing 44 is a fugitive, or temporary bond, as ultrasonic bonding is used later in the process to couple wing 44 to topsheet 40. Also preferably, adhesive 26' on wing 44 is present outside of a region intended for ultrasonic bonding to topsheet 40. Although fugitive adhesive 26' is preferred, it is optional, as vacuum present on the assembly line 12 can in some instances provide holding force sufficient to retain wings 44 against web 40 during processing.

As will be discussed later, in a preferred embodiment, first and second wing member portions 46, 48 of an individual wing member 44 ultimately end up on adjacent absorbent articles 100; that is, in a preferred embodiment, the wing members 44 preferably end up divided into two sections 46 and 48; first wing member portion 46 on one absorbent article 100, and second wing member portion 48 on a different absorbent article 100. Stated another way, in a preferred embodiment, portions of two individual wing members 44 can be used to form a single absorbent article 100. In a preferred production technique, one wing member 44 bridges two adjacent products 100 during production. A center of wing patch 44 (in the cross direction) is region at which a future knife cut is placed when absorbent articles 100 are cut to discrete. During production, adjacent products 100 are made discrete, dividing each wing member 44 into two sections 46 and 48, which will become left/right wings on adjacent products 100.

Still referring to FIG. 1 and also to FIG. 2B, a first wing-release paper web 60 is provided and adhesive 26 is applied by an adhesive applicator 24 in a predetermined pattern. Release paper typically has silicone coating so that adhesive cannot aggressively stick to it. In preferred embodiments, release paper as used in the present invention is used to prevent adherence of absorbent articles 100 in an unintended fashion. In use, absorbent articles 100 are provided with release papers which are removed, exposing adhesive surfaces for in-use adherence of absorbent articles 100 in desired places. As such, release papers 62 (and as later described, release papers 66) typically carry adhesive to wings 44, and also serve to cover adhesive 26 until intended product use. The first wing-release paper web 60 is then processed through the first release-paper slip-cutter 16 to provide individual and spaced first wing-release paper members 62. Preferably, each first wing-release paper member 62 is adhered to a respective wing member 44 on the first wing member portion 46 (FIG. 3), at or near a trailing edge of wing member 44 when considered in the machine direction 90. It should be noted that although reference is made to a trailing edge in the process, the process could easily be used to apply the release paper 62 to a leading edge of wing member 44 (to in effect, create right handed or left handed opening products in use). Also preferably, release paper 62 carries a single strip of adhesive 26 either from edge to edge or close-to-edge to close-to-edge of release paper 62 in the cross-machine direction. In use, release paper 62 can carry away adhesive 26 when removed from the article 100.

Figure 3:
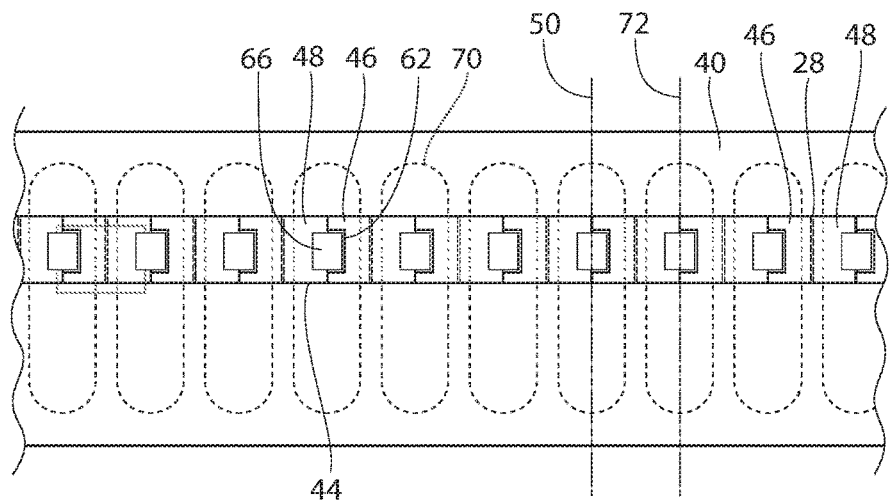
FIG. 3 is a top plan view of an absorbent article according to the present invention along the location indicated in FIG. 1 and FIGS. 2-1 and 2-2.
Figure 4:
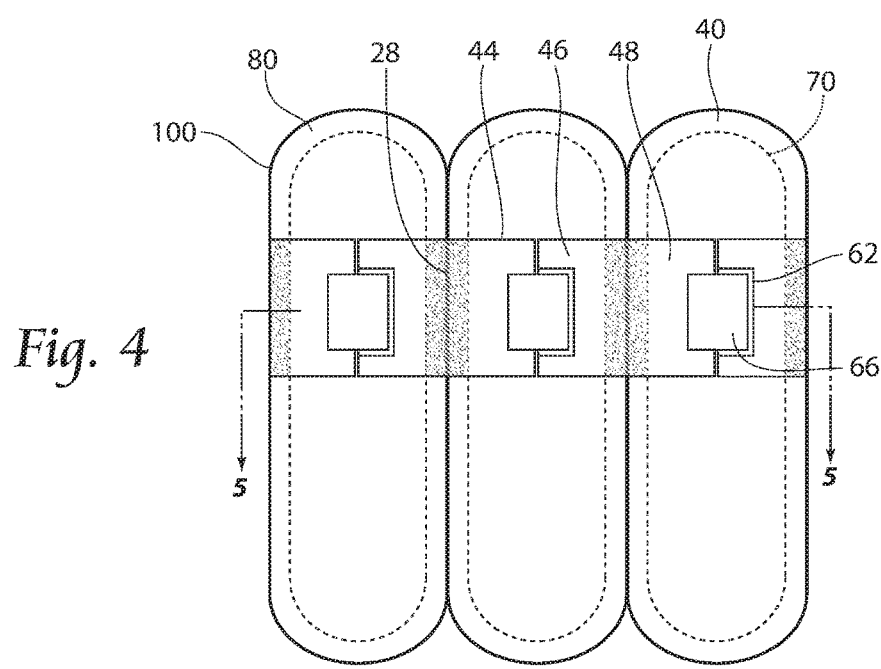
FIG. 4 is a top plan view of the absorbent article according to the present invention at the location indicated in FIGS. 2-1 and 2-2.
Figure 5:
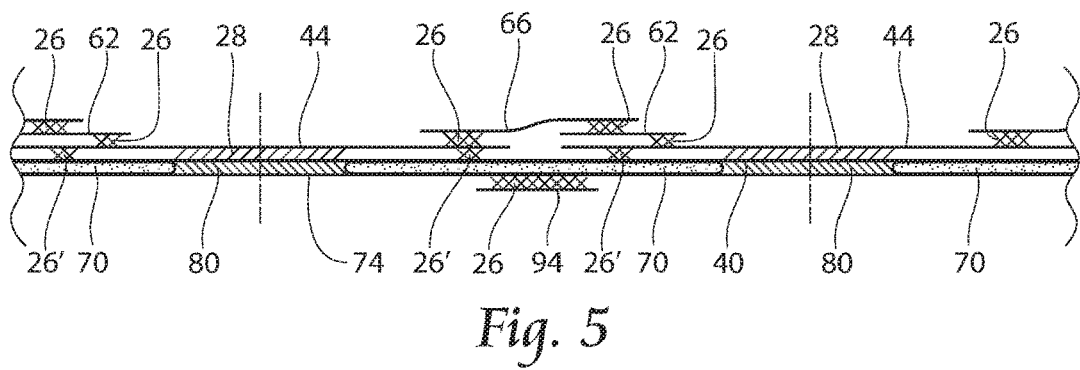
FIG. 5 is a cross sectional view of a preferred embodiment of the absorbent article shown in FIG. 4.

Still referring to FIG. 1, and also now to FIG. 2C, a second wing-release paper web 64 is provided and adhesive 26 is applied by an adhesive applicator 24 in a predetermined pattern. The second wing-release paper web 64 is then processed through the second release-paper slip-cutter 18 to provide individual and spaced second wing-release paper members 66. Preferably, each second wing-release paper member 66 is adhered to a respective wing member 44 onto the first wing-release paper member 62 (itself carried by first wing member portion 46 (FIG. 3), at or near a trailing edge of wing member 44), and then second wing-release paper member 66 overlaps adjacent wing members 44, and is carried by a leading edge of a trailing wing member 44 in the process, as can be seen in FIGS. 3-5. In such a configuration, second wing-release paper members 66 preferably carry adhesive 26 in two places of advancement in the machine direction, as see in cross-section in FIG. 5. In a preferred embodiment, adhesive 26 is carried by second wing-release paper member 66 toward a leading edge of second wing-release paper member 66 to facilitate coupling with first wing-release paper member 62 and toward a trailing edge to facilitate coupling with wing member 44 (see FIG. 5). Again, also preferably, release paper 66 carries these strips of adhesive 26 either from edge to edge or close-to-edge to close-to-edge of release paper 66 in the cross-machine direction.

The combination of topsheet 40, wing members 44, first wing-release paper members 62, and second wing-release paper members 66 continue down the first assembly line 12. The anvil 20 and ultrasonic horn 22 then combine to form an ultrasonic bond 28 of the wing members 44 and the topsheet 40 preferably at a location bisecting first and second wing member portions 46, 48 (see, e.g., FIG. 4). Additionally or alternatively, other forms of bonding now known or later developed may perform the step of bonding the wing members 44 to the topsheet 40 and still be within the purview of the present invention.

Concurrently with the process occurring along the first assembly line 12, a pulp core 70 is being formed and a backsheet 74 is provided along the second assembly line 30. The core forming drum 32 receives pulp (not shown) and/or superabsorbent polymer, and in many instances a combination of both, and forms individual cores 70 each having a core longitudinal center line 72 (see FIG. 3). Cores are produced as shown in FIG. 2E, preferably first fluffed, second debulked, and third embossed. The cores 70 are spaced apart a predetermined distance. The absorbent articles 100 are oriented with the core center line 72 transverse, or perpendicular, to the machine direction 90. This orientation increases the number of articles 100 processed over a distance traveled in the machine direction of an assembly line. It also increases the number of articles 100 produced over a given period of time at a given machine speed.

Typically, absorbent cores have an oblong shape designed to fit underneath a crotch section of a wearer, generally extending from the front of a body, under the body and to the rear of the body. Because of this configuration around the body of a wearer, rectangular, oblong, T-shaped or hourglass cores are commonly formed to be form fitting and comfortable. With respect to feminine hygiene products, cores are often hourglass shaped or elongated oval in shape. With regard to the present invention, a preferred core 70 is longer than it is wide, as depicted for example in FIGS. 3 and 4.

Additionally or alternatively, the cores 70 may be formed in any other manner now known or later developed, including for example, through a die-cutting process (not shown).

Still referring to FIG. 1, backsheet release paper web 92 is drawn past adhesive applicator 24 receiving adhesive 26, severed into individual backsheet release papers 94, and coupled to an underside of backsheet web 74. This process is also shown in FIG. 2D.

As shown in FIG. 1 the pulp cores 70 are adhered to the backsheet 74 with adhesive 26 from an adhesive applicator 24 prior to being combined with the topsheet 40. In a preferred embodiment, construction adhesive can be applied in full coverage by adhesive spray means to hold core 70 to backsheet 74. Additionally (and optionally and alternatively), as shown in FIG. 2-1, the pulp cores 70 may be adhered by adhesive, or other types of bonding to the topsheet 40 prior to combining the topsheet 40 and the backsheet 74. In any event, each core center line 72 is preferably aligned with a corresponding border line 50 separating neighboring wing members 44 as shown in FIG. 3.

Referring now to FIG. 2-1, an additional plan process view of the process shown in FIG. 1, and processes occurring after those shown in FIG. 1, is shown. Continuing from FIG. 1, the combination of topsheet 40 and backsheet 74, wings 44, first release papers 62, second release papers 66, backsheet release paper 94 and accompanying adhesives continue onward together as shown in FIG. 2-1.

Referring now to FIG. 2-2, after the topsheet 40 (carrying its associated product components) and backsheet 74 (carrying its associated product components) are introduced to one another, preferably following the step of bonding the wings 44 to the topsheet 40 as shown in FIG. 1, a perimeter seal 80 is formed, preferably by at least one of a heat bond, a pressure bond and an ultrasonic bond, indicated at bond 80. Referring now to FIG. 4, perimeter seal 80 forms a boundary about cores 70.

Still referring to FIG. 2-2, a final die-cut is provided to form a plurality of absorbent articles 100 according to the present invention as shown in FIG. 4. The absorbent articles 100 are then spaced apart, after which they preferably receive a web of pouch material for individual packaging. Individual products 100, now carried by a pouch web, are then folded along with the pouch web, and the pouch web is crimped about the products 100. The pouch web is then itself cut to carry an individually packaged article 100, and the individually packaged articles (now carried in a pouch) can be stacked packaged as desired.

Referring now to FIG. 5, a cross-sectional view of a preferred embodiment of the absorbent article shown in FIG. 4 is shown. Vertical dashed lines represent areas in which the final die cut of FIG. 2-2 can be employed to sever wings 44 (into their left portion 48 and right portion 46, see FIG. 4), topsheet 40, and backsheet 70, resulting in individual and now distinct products 100.

Figure 6:
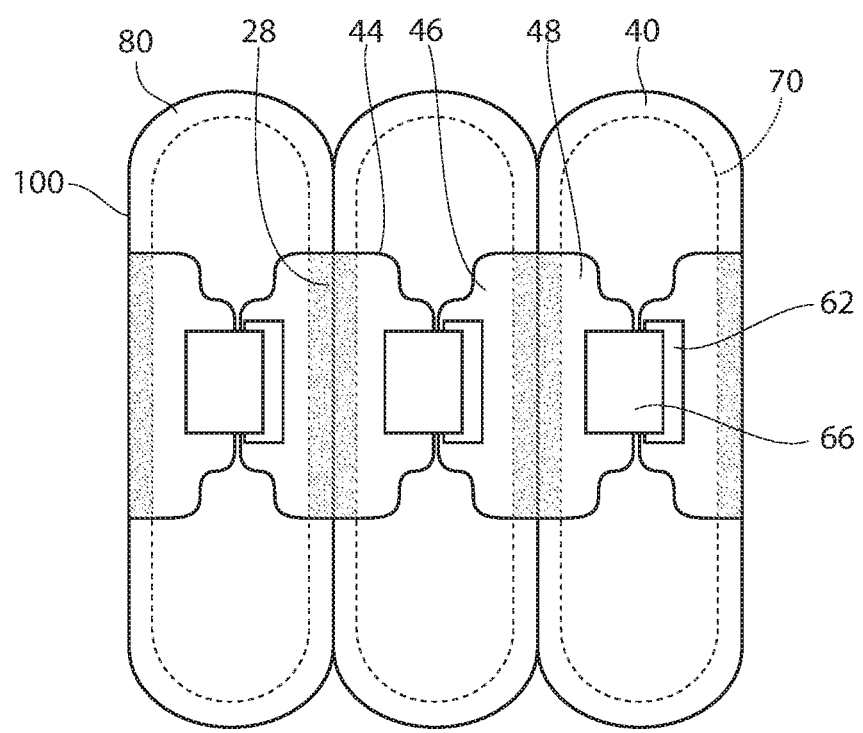
FIG. 6 is a top view of an alternate wing arrangement for use on the absorbent article.

Referring now to FIG. 6, a top view of an alternate wing 44 arrangement for use on the absorbent article 100 is shown. As can be seen, wings 44 are not necessarily rectangular (as shown for instance with reference to FIGS. 2-4) but can be contoured, shaped or formed by die cutting or otherwise as desired.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

The invention claimed is:

1. A method of producing a disposable product, the method comprising:
    coupling a first wing component to a first side of a topsheet web of material traveling in a machine direction;
    coupling a second wing component to the first side of the topsheet web of material adjacently to the first wing component in the machine direction;
    coupling a first base release paper to the first wing component; and
    coupling a second base release paper to the second wing component and to the first base release paper.

2. The method of claim 1 further comprising:
    coupling an absorbent core to a backsheet web of material traveling in the machine direction; and
    coupling the topsheet web of material to the backsheet web of material, wherein the absorbent core is positioned between the topsheet and the backsheet.

3. The method of claim 2 further comprising severing the topsheet web of material to create a discrete disposable product comprising the first and second wing components overlying the absorbent core.

4. The method of claim of claim 2, wherein the absorbent core has a length dimension and a width dimension less than said length dimension, wherein the length dimension is oriented transversely to the machine direction.

5. The method of claim 1 further comprising releasably coupling a backsheet release paper to an underside of the backsheet web.

6. A method of making a disposable product, the method comprising:
    coupling a plurality of wings to a top side of a topsheet web traveling in a machine direction;
    releasably coupling a first release paper to a first edge portion of a first wing of the plurality of wings; and
    releasably coupling a second release paper to the first release paper and to a first edge portion of a second wing of the plurality of wings adjacent to the first wing.

7. The method of claim 6 further comprising:
    coupling a backsheet web traveling in the machine direction to the topsheet web;
    cutting the topsheet web and the backsheet web to create a discrete disposable product, wherein cutting the topsheet web and the backsheet web comprises:
        cutting through the topsheet web, the backsheet web, and the first wing at a first cutting location positioned between the first edge portion of the first wing and a second edge portion of the first wing opposite the first edge portion of the first wing; and cutting through the topsheet web, the backsheet web, and the second wing at a second cutting location positioned between the first edge portion of the second wing and a second edge portion of the second wing opposite the first edge portion of the second wing.

8. The method of claim 6 further comprising:
positioning a core and a backsheet adjacently to the topsheet, the core having a length dimension and a width dimension less than said length dimension, wherein the length dimension is oriented transversely to the machine direction;
coupling the topsheet to the backsheet, wherein the core is positioned between the topsheet and the backsheet; and
severing said topsheet and said backsheet to create an absorbent article comprising the core and the first and second wings.

9. The method of claim 8 further comprising bonding the core to one of the topsheet and the backsheet.

10. The method of claim 8, wherein the first wing comprises a second edge portion opposite the first edge portion of the first wing;
wherein the second wing comprises a second edge portion opposite the first edge portion of the second wing; and
wherein the method further comprises severing the topsheet and the backsheet at a first position between the first and second edges of the first wing and at a second position between the first and second edges of the second wing to produce an absorbent article.

11. A method of manufacturing comprising:
coupling a plurality of wing members to a top side of a topsheet web traveling in a machine direction, wherein each wing member of the plurality of wing members comprises a first portion and a second portion, and wherein the first portion of each wing member coupled to the top side of the topsheet web is positioned adjacently to the second portion of an adjacent wing member coupled to the top side of the topsheet web;
coupling a backsheet web traveling in the machine direction to the topsheet web;
cutting the topsheet web and the backsheet web to create a first discrete disposable product, wherein cutting the topsheet web and the backsheet web comprises:
cutting through the topsheet web, the backsheet web, and a first wing member of the plurality of wing members at a first cutting location positioned between the first portion of the first wing member and the second portion of the first wing member; and
cutting through the topsheet web, the backsheet web, and a second wing member of the plurality of wing members at a second cutting location positioned between the first portion of the second wing member and the second portion of the second wing member.

12. The method of claim 11 further comprising coupling a first base release paper to the first portion of the first wing component; and
coupling a second base release paper to the second portion of the second wing component and to the first base release paper.

13. The method of claim 12 further comprising:
cutting the first base release paper from a first wing-release paper web; and
cutting the second base release paper from a second wing-release paper web.

14. The method of claim 11, wherein the second wing member is adjacent to the first wing member in the machine direction.

15. The method of claim 11 further comprising positioning an absorbent core between the topsheet web and the backsheet web.

16. The method of claim 15 wherein the absorbent core has a length dimension and a width dimension less than said length dimension, wherein the length dimension is oriented transversely to the machine direction.

17. The method of claim 15 further comprising forming a perimeter seal about the absorbent core through at least the topsheet web, the backsheet web, and the first and second wing members.

18. The method of claim 17, wherein forming the perimeter seal comprises forming the perimeter seal via one of a heat bond, a pressure bond, and an ultrasonic bond.

19. The method of claim 11 further comprising cutting the plurality of wing members from a wing material.

20. The method of claim 11 further comprising cutting the topsheet web and the backsheet web to create a second discrete disposable product, wherein cutting the topsheet web and the backsheet web to create the second discrete disposable product comprises:
cutting through the topsheet web, the backsheet web, and a third wing member of the plurality of wing members at a third cutting location positioned between the first portion of the third wing member and the second portion of the third wing member; and
wherein the second discrete disposable product comprises the second portion of the second wing member cut during creation of the first discrete disposable product.

* * * * *